United States Patent [19]

Ibsen

[11] Patent Number: 5,288,500
[45] Date of Patent: Feb. 22, 1994

[54] ORAL COMPOSITION CONTAINING PARTICLES COMPRISING AN ACTIVE SUBSTANCE

[75] Inventor: Lars S. Ibsen, Frederiksberg, Denmark

[73] Assignee: Benzon Pharma A/S, Hvidovre, Denmark

[21] Appl. No.: 857,515

[22] Filed: Mar. 25, 1992

Related U.S. Application Data

[60] Division of Ser. No. 526,671, May 21, 1990, Pat. No. 5,147,655, which is a continuation of Ser. No. 166,638, Mar. 11, 1988, abandoned.

[30] Foreign Application Priority Data

Mar. 13, 1987 [DK] Denmark ............................. 1302/87

[51] Int. Cl.$^5$ ............................................. H61K 9/16
[52] U.S. Cl. .................................... 424/489; 424/490; 424/491; 424/492; 424/493; 424/494; 424/495; 424/496; 424/497; 424/499; 424/500; 424/501; 514/937
[58] Field of Search ............... 424/489, 490, 493, 494, 424/495, 497, 499

[56] References Cited

U.S. PATENT DOCUMENTS

| | | | |
|---|---|---|---|
| 2,650,895 | 9/1953 | Wallenmeyer et al. | 167/81 |
| 3,056,728 | 10/1962 | Ohtaki | 167/81 |
| 3,079,303 | 2/1963 | Raff et al. | 167/82 |
| 3,445,563 | 5/1969 | Clegg et al. | 424/35 |
| 4,221,778 | 9/1980 | Raghunatha | 424/31 |
| 4,254,100 | 3/1981 | Keller et al. | 424/37 |
| 4,305,933 | 12/1981 | Wiczer | 424/180 |
| 4,393,076 | 7/1983 | Noda et al. | 424/317 |
| 4,572,833 | 2/1986 | Pederson et al. | 424/20 |
| 4,704,268 | 11/1987 | Kifune | 424/488 |
| 4,762,702 | 8/1988 | Gergely et al. | 424/44 |
| 4,882,169 | 11/1989 | Ventouras | 424/493 |
| 4,886,669 | 12/1989 | Ventouras | 424/493 |

FOREIGN PATENT DOCUMENTS

| | | |
|---|---|---|
| 0166766 | 4/1984 | Australia . |
| 0084190 | 7/1983 | European Pat. Off. . |
| 0136013 | 4/1985 | European Pat. Off. . |
| 0138540 | 4/1985 | European Pat. Off. . |
| 0153105 | 8/1985 | European Pat. Off. . |
| 0190826 | 8/1986 | European Pat. Off. . |
| 0207032 | 12/1986 | European Pat. Off. . |
| 55-118414 | 9/1980 | Japan . |
| 57-058609 | 4/1982 | Japan . |
| 59-063147 | 4/1984 | Japan . |
| 60-016912 | 1/1985 | Japan . |
| 60-016913 | 1/1985 | Japan . |
| 61-122211 | 6/1986 | Japan . |
| 0968443 | 9/1964 | United Kingdom . |
| 2041958 | 9/1980 | United Kingdom . |
| 2100269 | 12/1982 | United Kingdom . |

*Primary Examiner*—Paul R. Michl
*Assistant Examiner*—James M. Spear
*Attorney, Agent, or Firm*—Bryan Cave

[57] ABSTRACT

An oral composition which is adapted to be dispersed in an aqueous carrier substantially immediately prior to administration comprises a multiplicity of particles comprising an active substance, the particles being combined with one or more gelling or swelling agents capable of forming a viscous medium around the particles in an aqueous carrier as well as being provided with a masking surface layer when dispersed in the aqueous carrier. This serves to mask uneven surfaces on the particles and prevent them from adhering to oral mucosa when the composition is ingested and thus makes it easier to administer large dosages of an active substance. The masking surface layer is preferably provided by an increased viscosity of the viscous medium in the immediate vicinity of the particles relative to the viscosity of the surrounding aqueous carrier.

A ready-to-use composition is prepared by mixing the composition with an aqueous carrier substantially immediately prior to administration of the composition.

16 Claims, No Drawings

ORAL COMPOSITION CONTAINING PARTICLES COMPRISING AN ACTIVE SUBSTANCE

This is a divisional, of U.S. application Ser. No. 07/526,671 filed May 21, 1990, U.S. Pat. No. 5,147,655 which is a continuation of U.S. application Ser. No. 07/166,638 filed Mar. 11, 1988 (abandoned).

FIELD OF INVENTION

The present invention relates to an oral composition containing particles comprising an active substance combined with a gelling or swelling agent, a process for preparing such a composition as well as a method of preparing a ready-to-use composition by adding an aqueous carrier to said composition.

TECHNICAL BACKGROUND

The most common dosage forms currently employed for oral administration of active substances are tablets and capsules. However, in recent years awareness of the drawbacks of using these dosage forms has increased. Thus, tablets and capsules are generally less suitable for administering large dosages of an active substance as large tablets or capsules are difficult to ingest, or the large dosages necessitate the administration of several tablets or capsules at a time, resulting in impaired patient compliance. Furthermore, patents often have to take several different tablets or capsules containing different active substances either at a time or at specific intervals during the day. This also leads to reduced patient compliance.

Active substances may alternatively be formulated as powders or granules to be admixed with a liquid in a container such as a glass before administration, thereby overcoming the difficulties involved in administering large dosages of an active substance in tablet or capsule form. However, with such a formulation other problems arise, especially when the active substance in question is not dissolved in the liquid, but is present in particulate form. In such cases, the particles tend to sink to the bottom of the glass and stay there even when the contents of the glass are stirred before the glass is upended for ingestion of the liquid or to adhere to the sides of the glass when the liquid is ingested. In this way a certain amount of the active substance will remain in the glass giving rise to an unacceptable variation in the dosage of the active substance actually ingested by those to whom it is administered in this form. Furthermore, such granules or particles often have an unpleasant feel in the mouth as they typically have an irregular shape which makes them feel gritty, and they also tend to adhere to oral mucosa after the liquid carrier has been washed down. Such a dosage form therefore also tends to lead to reduced patient compliance.

Chewable tablets are not a viable alternative in most cases as they may be difficult to masticate especially for older people and young children and, importantly, as most drugs have an extremely unpleasant taste. If the active substance is formulated in controlled-release form as particles containing the active substance coated with a controlled-release coating, it cannot be compounded into chewable tablets as this would destroy the controlled-release effect.

Therefore, there is a need of a formulation of active substances permitting the administration of large dosages at a time and making it easy to ingest the dosage of the active substance, and which furthermore provides an easy way of administering several active substances in the same dosage.

SUMMARY OF THE INVENTION

The purpose of the present invention is to provide an oral composition which overcomes the drawbacks of conventional oral formulations of active substances by combining particles containing an active substance with a gelling or swelling agent which is hydrated in the presence of an aqueous carrier to form a viscous medium surrounding the particles. This increases the viscosity of the aqueous carrier which contributes to facilitating the ingestion of the composition when an aqueous carrier is added to it prior to administration.

Accordingly, the present invention relates to an oral composition which is adapted to be dispersed in an aqueous carrier substantially immediately prior to administration and which comprises a multiplicity of particles comprising an active substance, said particles being combined with a gelling or swelling agent capable of forming a viscous medium around the particles in an aqueous carrier as well as being provided with a masking surface layer when dispersed in the aqueous carrier.

The present invention further relates to a method of preparing a ready-to-use composition which comprises a multiplicity of particles comprising an active substance, the particles being combined with a gelling or swelling agent, the method comprising mixing said particles combined with the gelling or swelling agent with an aqueous carrier substantially immediately prior to the administration of the composition to form a viscous medium of the gelling or swelling agent around the particles and to provide a masking surface layer on the particles. The resulting viscous suspension of the particles will then be ready for administration.

In an alternative embodiment, the present invention provides a method of preparing a ready-to-use composition which comprises a multiplicity of particles comprising an active substance, the method comprising adding a gelling or swelling agent to an aqueous carrier to form a viscous medium and mixing said particles with the viscous medium substantially immediately prior to administration of the composition to form a viscous medium of the gelling or swelling agent around the particles and to provide a masking surface layer on the particles. This embodiment includes admixture of the particles comprising the active substance with a pre-mixed viscous gel medium of the gelling or swelling agent, i.e. the gel is prepared beforehand and provided to the user as such for admixture with the particles comprising the active substance. Alternatively, the gelling or swelling agent may be provided in dry form and may be gelled in the aqueous carrier immediately prior admixture with the particles comprising the active substance.

Although oral compositions comprising particles of an active substance suspended in a viscous aqueous vehicle have previously been described (cf. European Published Specification No. 138 540 U.S. Pat. No. 485591), these compositions are formulated as ready-to-use suspensions from the outset and are handled, transported and stored as such, whereas the compositions of the present invention are prepared and stored in dry form and are not converted to ready-to-use suspensions until they are to be used at which time they are admixed with the aqueous carrier or the pre-mixed gel. This may in some cases present the important advantage over the known premanufactured suspensions that the composition of the present invention has an increased storage stability and permits a wider range of active substances to be incorporated therein, as most active substances at present contemplated to be administrable in these compositions are in fact unstable in the presence of an aqueous carrier or become unstable within a relatively short period of time. The composition of the invention also shows improved packaging, handling and transportation properties due to the fact that the ready-to-use suspension is prepared in situ either by the end user or by medical staff. Furthermore, it is easy to measure out exact dosages (reproducible amounts of) of the active substance in the composition of the invention, because the particles comprising the active substance are present in the composition in dry form (which is easier to measure out), or optionally in unit dosage form, until substantially immediately prior to administration (i.e. from about a few seconds to about an hour), the particles comprising substantially uniform amounts of active substance, whereas exact dosages of the active substance are difficult to obtain from ready-made suspensions since there is no homogeneous admixture of the active substance in the ready-made suspensions and since precise dosages are difficult to measure out for both patients and nursing staff.

The compositions of the invention make it possible to administer large individual dosages of an active substance in that they do not impose the limitations with respect to size imposed by conventional tablets or capsules. Consequently, the compositions of the inventions are particularly well suited for administration of active substances which are generally administered in large dosages. Furthermore, according to the invention, the masking surface layer formed on the particles when the composition is made ready for use provides the particles with a smooth surface which serves to mask uneven surfaces on the particles comprising the active substance and prevent them from adhering to oral mucosa, or to containers where the ready-to-use compositions are prepared, and may also contribute to masking any unpleasant taste of the active substance. The composition of the present invention is hereby distinguished from the ready-to-use product disclosed in FR 2 473 307 which comprises powdered dihydroxybutylether to be dispersed in a gelling agent. In this dispersion, a slurry is formed of dihydroxybutyl ether particles in a viscous medium of the gelling agent. This medium has a uniform viscosity throughout the dispersion and hence does not show the advantageous feature of forming a smooth surface layer substantially around each particle of the active substance. The particles of the active substance may therefore be expected to separate from the viscous medium and either sediment in the container in which the dispersion is made, after standing for a certain period of time, or adhere to its walls or to oral mucosa when the product is ingested. It has also been found that these dispersions require a disproportionally large amount of liquid relative to the amount of active substance in order to obtain an adequate dispersion of the gelling agent, whereas the compositions of the present invention may include any desired amount of active substance without necessitating a corresponding increase in the amount of liquid required to prepare the ready-to-use composition.

DETAILED DISCLOSURE OF THE INVENTION

It is contemplated that the masking surface layer on the particles may be provided by for instance a substance which will produce a foam around the particles on dispersion thereof in the aqueous carrier. However, in a currently preferred embodiment of the present invention, the masking surface layer on the particles containing the active substance is provided by an increased viscosity of the viscous medium in the immediate vicinity of the particles relative to the viscosity of the surrounding aqueous carrier. In other words, according to this embodiment, the viscous medium forms a layer of a gelled mass with a higher viscosity than the rest of the viscous medium, this gelled mass surrounding the particles, and substantially each particle, of the composition.

In accordance with the principles of the present invention, the gelling or swelling agent is a vital component of the present composition. Gelling agents are usually substances which form colloidal dispersions in an aqueous environment, the colloidal particles forming a three dimensional network or grid-like structure throughout the liquid phase. In the present context, the term "gelling agent" includes sols and solid-in-liquid suspensions. It should be noted that the term "gelling or swelling agent" is also intended to include the viscous medium (gel) formed by the agent when it is dispersed in the aqueous carrier (which may be any suitable liquid such as water, juice or milk).

Although the viscosity of the composition on dispersion in the aqueous carrier is not particularly critical, the gelling or swelling agent should be present in a concentration which, on the one hand, is sufficient to impart a viscosity to the viscous medium surrounding the particles which is adequate to mask their gritty feel, but which, on the other hand should not be so high that it will result in a viscosity which might create difficulties when the composition dispersed in the aqueous carrier is to be emptied from the container in which it has been mixed, giving rise to undesirable dosage variations. In other words, the gelling or swelling agent should preferably not be one which forms a solid or nearly solid gel throughout the composition although as mentioned above, the viscous medium formed by the gelled substance preferably has a higher viscosity in the immediate vicinity of the particles.

It should be noted that although the consistency of the aqueous carrier when admixed with the gelling or swelling agent to a large extent depends on the concentration in which the gelling or swelling agent is present in the ready-to-use composition, the desired viscosity may often be obtained by adjusting the amount of gelling or swelling agent combined with the particles comprising the active substance, by selecting a gelling or swelling agent with a specific degree of polymerization, or by mixing high-viscous and low-viscous gelling or swelling agents in specific ratios to obtain the desired viscosity. An advantageous viscosity of the ready-to-use composition may be from that of a relatively thin oil to that of a relatively thick cream or paste.

Furthermore, the viscous gel medium may be one which becomes less viscous or dissolves under the conditions, especially with respect to pH and enzymes, prevailing in the stomach so that it does not influence the release of the active substance from the particles. On the other hand, the gelling or swelling agent may advantageously be one which is stable for a sufficient period of time in a certain pH-range. Apart from this, the gelling or swelling agent should preferably be one which does not depend on heating in order to form a satisfactory gel, and should preferably be one which may be used in low concentrations to produce a desired viscosity. It should preferably be possible to regulate the properties of the gel with respect to viscosity, syneresis, etc. by external means such as adjusting the pH of the gel, or adding a reagent to the composition or the aqueous carrier to react with the gelling or swelling agent and hence influence the properties of the gel (vide the discussion below).

Examples of useful gelling or swelling agents are hydrophilic polymers selected from natural or semi-synthetic polysaccharides such as pectin, agar, dextran, carageenan, tragacanth gum, locust bean gum, acacia gum, guar gum, ghatti gum, xanthan gum, alginic acid or derivatives thereof such as sodium alginate, or a cellulose derivative, e.g. methylcellulose, carboxymethylcellulose, sodium starch glycollate, sodium carboxymethylcellulose, hydroxyethyl methylcellulose, hydroxypropyl methylcellulose and microcrystalline cellulose. Other useful gelling or swelling agents may be selected from inorganic substances such as silica and silicates (e.g. aluminium silicate, magnesium silicate, aluminium magnesium silicate and sodium silicate) and aluminium hydroxide, proteins such as gelatin or casein and synthetic polymers such as acrylic polymers (acrylates), carboxpolymethylene, polyalkylene glycols, e.g. polyethylene glycol, and polyvinylpyrrolidone. Mixtures or different grades of the gelling or swelling agents may also be employed. All of these gelling or swelling agents may be dispersed in water (i.e. an aqueous carrier) and the viscosity of the gel formed by the gelling or swelling agents may be subject to control by regulating the chemical equilibria determining the concentration of reactants in the viscous medium surrounding the particles comprising the active substance. The concentration of the gelling or swelling agent will of course, in each case, depend on the desired viscosity of the ready-to-use composition, the gel-forming properties of the gelling or swelling agent employed, etc. However, a realistic concentration of the gelling or swelling agent for obtaining a suitable consistency of the composition is usually in the range of 0.05-20%, preferably 0.1-10%, in particular 0.2-5%, by weight of the ready-to-use composition.

In one embodiment of the composition of the invention, the particles may simply be admixed with the gelling or swelling agent in dry form. In an alternative embodiment, the particles containing the active substance and the powder or particles of the gelling or swelling agent may be kept separately: when preparing the ready-to-use composition of the invention, the gelling or swelling agent may, in this case, be dispersed in the aqueous carrier to form the viscous medium (gel) before admixture with the particles containing the active substance. It may furthermore be possible to prepare a ready-made dispersion of the gelling or swelling agent in the aqueous carrier during manufacture of the composition; this viscous gel is then kept separate from the particles comprising the active substance which are invariably stored in dry form until the composition is to be administered. It may occasionally be an advantage to prepare a ready-made dispersion of the gelling or swelling agent as some such agents are not instantly dispersed when added to an aqueous carrier, but require a certain period of time to be uniformly dispersed in the carrier and form a gel of a satisfactory viscosity. If the resulting gel has too high a viscosity to permit an easy admixture with the particles comprising the active substance, a further quantity of aqueous carrier may be added until the desired viscosity is obtained.

In another embodiment of the composition of the invention, the particles may be granulated together with the gelling or swelling agent. The granulation is performed by conventional means, using well-established methods, excipients, etc.

In yet another embodiment of the composition of the present invention, the particles may be coated with a coating which is composed of at least one layer comprising the gelling or swelling agent. In this case, no further modification of the composition in the form of specific reagents is needed in order to obtain a more highly viscous medium around the particles.

The particles may furthermore be provided with a coating layer of a film mediating controlled release of the active substance from the particle (e.g. a crystal or granule) comprising it, i.e. typically a diffusion or enteric film coating. Such a controlled-release coating is usually provided when the active substance is one that acts as a local irritant on gastrointestinal mucosa, or when it is desired to obtain a prolonged effect of the active substance, in accordance with principles which are well known to those skilled in the art. A controlled-release coating is, however, not an obligatory feature of the composition of the invention. Thus, the coating may also be a water-soluble coating which serves to contain viscosity-regulating components or to mask an unpleasant taste of the active substance.

As explained above, the gelling or swelling agent serves to mask any grittiness of the particles resulting from an uneven surface thereof, and to provide a slippery surface which makes the particles easier to swallow. This is particularly important when the particles comprising the active substance are above a certain size. Thus, the particles comprising the active substance typically have a size in the range of about 0.05-7 mm, for instance about 0.1-3 mm.

In the present context, the term "active substance" is intended to indicate not only drugs, but all kinds of substances which may play a part in biochemical processes in the body. Hence, the active substance may be selected from drugs, vitamins, micronutrients and macronutrients. The composition of the invention is particularly advantageous for formulating bulky active substances since this dosage form is not limited to a specific size which is possible to swallow, contrary to what is the case with tablets or capsules. Active substances may be bulky either because large quantities of the active substance are required per dosage to be administered or because the active substance itself is bulky or has to be formulated with one or more bulky excipients. Examples of bulky active substances are naproxen, ibuprofen, paracetamol, acetylsalicylic acid, potassium chloride, ampicillin, bacampicillin, cimetidine, bevantolol and antacids such as magnesium oxide/aluminium amino acetate, which all require dosages of 200.3000 mg per dosage, the dosages being administered up to several times a day. Other examples are vitamins (such as Vitamin C), micronutrients (e.g. minerals such as Ca, Mg, Na, Fe, F, K, etc.) and combinations thereof as in conventional vitamin/mineral supplements, and macronutrients such as dietary fibers, carbohydrates (e.g. sugars) and proteins. Examples of drugs formulated with bulky excipients are drugs coupled to carriers such as cyclodextrins, antibodies, lectins, globulins, etc.

The possibility of administering large dosages of an active substance obtained by the composition of the invention has also made it feasible to combine two or more active substances in the same composition, provided that they are compatible, greatly simplifying dispensing and administration procedures in hospitals, nursing homes and other institutions where patients at present often have to ingest several tablets or capsules, each containing a different active substance, at a time. It is contemplated that the entire daily dosage of drugs and optionally other active substances may be administered once or perhaps twice a day, provided that the active substances are compatible, and one or more of the active substances may suitably be provided in controlled-release form. Such an administration regimen would both lead to improved patient compliance and lighten the work load of hospital and similar staff.

As indicated above, it is preferred to provide the masking surface layer in the form of a somewhat thicker viscous gel medium in the immediate vicinity of the particles comprising the active substance in order to mask uneven surfaces effectively. Such masking may for instance be provided by coating the particles with a gelling or swelling agent which is not easily soluble in water. Alternatively, the composition may further comprise a substance which increases the viscosity of the viscous medium formed around the particles in the aqueous carrier by the gelling or swelling agent. This viscosity increasing substance may be included in the particles comprising the active substance. Alternatively, the viscosity-increasing substance may be included in a coating provided on the particles. The inclusion of such a viscosity-increasing agent in the composition will result in a thicker gel around the particles than in the remainder of the composition when it is admixed with the aqueous carrier, but this will nevertheless be a gel which disintegrates rather quickly after the composition has been ingested. Substances causing the medium to become more viscous around the particles may be substances which possess a specific redox potential or which form salts or chelates with the gelling or swelling agent or which increase the concentration of the gelling or swelling agent or change the binding properties in the gelling or swelling agent in the immediate vicinity of the particles.

Salt Formation

The viscosity increase in the immediate vicinity of the particles may be provided by direct salt formation by means of mono-, di- or tri-valent ions. The ions may be both cations and anions dependent on whether the gelling or swelling agents are cationic or anionic in nature. Examples of useful cations are metal ions such as Li, Na, K, Mg, Ca, Zn, Cu, Fe, Cr, Ni, Mn and Al, as well as $NH_4$. Combinations of these ions are also possible, e.g. Mg and Al as in aluminium magnesium silicate. Occasionally, the appropriate ion may be present in a gelling or swelling agent, e.g. Ca in calcium carboxymethylcellulose, Na in sodium alginate and sodium carboxymethylcellulose, K, Mg and Ca in acacia gum, $NH_4$, Na, K and Ca in carrageenan and Mg in magnesium silicate. Furthermore, various organic ammonium compounds such as triethanol ammoniumchloride may be employed together with carboxypolymethylene. Other ammonium ions may be formed by certain amino acids at a neutral or acid pH.

Examples of anions which are useful for the present purpose are Cl, Br, $SO_4$, $PO_4$, $NO_3$, $CO_3$ and a number of organic compounds such as salts of carboxylic acids, e.g. lactic, acetic, citric, acetyl, salicylic, benzoic, alginic, malic, stearic, palmitic, ascorbic and galacturonic acid, and optionally polymerizates of acids such as amino acids, as well as carboxyrethylcellulose. Apart from these. amino acids may be used, such as glutamic acid, aspartic acid, glycine etc. Amino acids primarily form cations at a neutral or slightly acid pH, but most amino acids exist as zwitterions even under slightly basic conditions.

When the local viscosity increase is obtained by means of salt formation. it may be possible to regulate the rate at which the more highly viscous gel is formed as well as the viscosity of the resulting gel by means of the pH of the aqueous dispersion of the gelling or swelling agent in the carrier, the particle size of the salt determining the surface area accessible to the aqueous carrier, or by employing mixtures of different salts, for instance different anions of the same metal ion or different metal ions. It is, for instance, characteristic that tri-valent ions form more highly viscous gels than di-valent ions. Inclusion of such different salts in different coating layers on the particles may be employed to achieve a more specific time-dependent gel formation.

Chelate Formation

The desired viscosity increase around the particles may also be obtained by means of chelate formation. Substances useful for this purpose may be the same as those discussed above with respect to salt formation. However, a chelating agent may also increase the viscosity together with substances which are not electrically charged, or the chelating agent may in itself give rise to a viscosity increase. The mechanism of chelate formation may be utilized to regulate gel formation. Thus, EDTA (ethylenediaminetetraacetic acid) may be included in the composition of the invention to control the concentration of, for instance, metal ions (such as those listed above) in the viscous medium by chelate formation. Other chelating agents which may be employed for the same purpose may be selected from a wide range of primarily organic compounds, including various polymers such as polyoxyethylenes, peptides, proteins, polysaccharides (starch and cellulose derivatives), polyesters, etc.

Redox Potential

According to the invention, an appropriate viscosity increase around the particles may also be obtained by including substances which due to a well-defined redox potential may be used to regulate equilibria between different oxidation stages of the same substance which may have different salt or chelate forming properties. It may be possible directly to influence a gelling or swelling agent containing redox sensitive groups, e.g. easily reducible acid groups or easily oxidizable hydroxy or amino groups. Substances having useful redox potential include Fe, Cu, Zn, Cr. Mn and Co. Furthermore, a number of organic substances may be employed, in particular complex biological substances such as cytochromes, hemoglobins, various enzymes such as enzymes involved in the citric acid cycle or the corresponding coenzymes or prosthetic groups, in order to achieve a specific redox potential. Some of these substances may also act as gelling agents, for instance polymers such as polysaccharides which may be included in the composition of the invention in oxidized or reduced form and reduced or oxidized, respectively, in the aqueous carrier to form the viscous medium.

Local Increase of Gel Concentration

This may be obtained by "removing water from the gelled gelling or swelling agent, resulting in a more highly concentrated gel. More specifically, removal of water may be achieved by applying a swelling, but water-soluble coating on the particles which coating swells in the presence of the aqueous carrier, attracting water from the surrounding gel which becomes more concentrated and hence more viscous.

Swelling agents which are useful for this purpose and which may be incorporated in a water-soluble film forming agent to form the swellable film may be substances used as conventional tablet disintegrants. Examples of such substances are starches such as corn or potato starch, cellulose derivatives such as sodium or calcium carboxymethylcellulose, methylcellulose, ethylcellulose, ethylhydroxyethylcellulose, microcrystalline cellulose, ethylmethylcellulose, hydroxyethylcellulose, hydroxyethylmethylcellulose, cellulose acetate phthalate, etc., other polysaccharides such as agar, alginate, pectin, acacia gum, tragacanth gum, xanthan gum, guar gum and ghatti gum, inorganic substances such as aluminium silicate, magnesium silicate, aluminium magnesium silicate, silica and various felspars, proteins such as gelatin and synthetic polymers such as carboxypolymethylene and polyvinylpyrrolidone (it will be noted that these substances are in many instances identical to the ones listed above as gelling or swelling agents).

Changing the Polarity of the Medium

A locally increased viscosity of the gelling or swelling agent may be obtained by including a surfactant in the composition of the invention, thus reducing the surface tension of the water in the aqueous carrier. Useful surfactants include polymers such as polyvinylpyrrolidone, polyethylene glycol and water-soluble polysaccharides, low molecular weight substances such as mono- or di-saccharides, alcohols such as ethanol and glycerol, amines such as amino acids, esters and amides such as acetylsalicylic acid and EDTA, detergents such as polysorbates, sodium lauryl sulphate and salts of fatty acids, e.g. palmitic, stearic, oleic or lauric acid, and phospholipids.

It should be noted that many of the substances mentioned above may act in different ways to increase the viscosity of the viscous medium around the particles so that it is not always possible to ascribe the viscosity increase to just one of the principles described above. In fact, the reactions which give rise to the viscosity increase are most often a combination of two or more of these principles.

If the particles are coated with a coating containing a viscosity-increasing substance, the coating may be controlled-release coating as defined above. This will make it possible to determine the release of the viscosity-increasing agent and hence the rate at which the highly viscous medium is formed by controlling the diffusion rate of the viscosity-increasing agent through the coating. Alternatively, the coating in which the viscosity-increasing agent is incorporated may be one which is independent of any intended controlled-release effect, for instance a water-soluble polymer.

Finally, the viscosity-increasing substance may be present in the aqueous carrier. In order to prevent formation of a highly viscous medium throughout the aqueous carrier, an acid, in particular a weak acid, may advantageously be present in the particles comprising the active substance or in a coating provided thereon. If so, the viscosity-increasing agent must be pH sensitive, which means that it should exert its viscosity-increasing activity in a certain pH range, its activity for instance resulting from its being soluble at a certain pH. When the acid is released from the particles or the coating thereon, the viscosity of the medium will be increased in the immediate vicinity of the particles. The acid may, for instance, be glutaminic acid, glucono delta lactone, tartaric acid, citric acid, phosphoric acids, carbonic acids, and buffers thereof.

If the viscosity.increasing substance is a sparingly soluble substance and is present in the particles or in a coating on the particles, an easily dispersed substance such as a chelating agent (e.g. sodium citrate which may be used in connection with di- or trivalent metal ions used for salt formation as described above) or an affinity chromatography or ion exchange resin may be added to the composition in a low concentration to be present in the aqueous carrier in the ready-to-use composition in order to provide a chemical retardation of gel formation by the sparingly soluble viscosity-increasing substance in the particles or in a coating provided on the particles, thus preventing the formation of a thick gel throughout the aqueous carrier.

It may be an advantage to provide the composition of the invention in a form that allows measuring out individual dosages of the active substance comprised in the particles in situ. Thus, particles comprising an active substance may be dispensed according to each patient's need, i.e. each dosage may be measured according to individual requirements, and two or more active substances may also be mixed in this way, if required. In this embodiment of the composition of the invention, particles comprising an active substance may be stored in separate containers for each active substance, and a dosage of each (at least one) active substance to be administered may be measured out into another container, typically a glass, and mixed with a measure of gelling or swelling agent in powder, tablet or pre-mixed form and aqueous carrier to a satisfactory viscosity. This way of dispensing an active substance permits greater flexibility and individual variety in the administration of active substances.

The composition of the invention may, however, also be provided in unit dosage form, typically a sachet, capsule or tablet containing a specific amount of particles comprising one or more active substances and optionally also a gelling or swelling agent. This may, however also be provided separately, either in dry form or as a pre-gelled dispersion in the aqueous carrier as indicated above. The unit dosage will usually contain at least 200 mg of the active substance and often more than that as no limitations as to the maximum amount of active substance that can be incorporated in each dosage is imposed by the present formulation, contrary to conventional capsules or tablets intended for being swallowed as such. If the composition of the present invention is formulated as a capsule or tablet, it is intended to be disintegrated in an aqueous carrier such as water before ingestion. In order to facilitate dispersion of the capsule or tablet contents in the aqueous carrier, it may be an advantage to include an effervescent agent such as sodium bicarbonate; this will also accelerate the dispersion of the gelling or swelling agent in the aqueous carrier when it is present in the composition in dry form.

The composition of the invention may further comprise conventional fillers or adjuvants such as disintegrants or lubricants as well as conventional, pharmaceutically acceptable flavouring or colouring agents. The filling of capsules and sachets and the compression of tablets are performed in a manner known per se.

The invention is disclosed in further detail in the following examples which should not be construed as limiting the invention in any way.

| MATERIALS AND METHODS | |
|---|---|
| Purified, crystalline sucrose | Supplied by Irma A/S, Denmark. |
| Paraffin | Ph. Nord. 63. |
| Isopropanol | DLS (Dansk Laegemiddel Standard - "Danish Drug Standard") |
| Acetyltributylcitrate | Citroflex ® A4; supplied by Pfizer A/S, Denmark |
| Ethylcellulose | NF XV |
| Colloidal silica | USP XXI |
| Colloidal aluminium magnesium silicate | Veegum ® PRO; supplied by Superfos Chemicals A/S |
| Citric acid, monohydrate | Ph. Eur. Suppl. 77 |
| Sodium citrate | Ph. Eur. III |
| Saccharin sodium | Ph. Nord. 63 II |
| Sodium chloride | Ph. Eur. I Suppl. 73, Suppl. 77. |
| Hydroxypropylmethylcellulose | Hypromellose 50 AB and Hypromellose 5 AB, USP XXI; Hypromellose 15, supplied by DAK, Denmark (in the following abbreviated to HPMC) |
| Propylene glycol | Ph. Eur. III |
| Polyvinylpyrrolidone | DLS 83 (in the following abbreviated to PVP) |
| Purified water | Ph. Eur. 2nd Ed., 8, 1980. |
| Polyplasdone XL | crosslinked PVP; supplied by GAF A/S, Ballerup, Danmark |
| Polyethylene glycol 6000 | Ph. Nord. 63 II (in the following abbreviated to PEG) |
| Dextrose | Ph. Eur. II |
| Sodium alginate | SOBALG FD 160, SOBALG FD 167 and SOBALG FD 170; supplied by Grindsted Products A/S, Denmark |
| Alginic acid | SOBALG PH 060, supplied by Grindsted Products A/S, Denmark, |
| Potassium chloride crystals | Ph. Eur. I, size fraction 0.2–0.6 mm |
| Calcium hydrogen phosphate | Ph. Eur. III |
| Microcrystalline cellulose | Avicel ® PH 101; DLS 83 |
| Acetylsalicylic acid crystals | Ph. Eur. I |
| Antifoam emulsion | supplied by DAK, Denmark |
| Magnesium stearate | Ph. Eur. III |
| Talc | Ph. Eur. III |
| Eudragit ® NE 30 D | A neutral acrylic acid ethyl ester/methacrylic acid methyl ester-copolymerizate in the ratio 70:30, MW >800,000, as a 30% aqueous dispersion, supplied by Rohm Pharma GmbH, Darmstadt, BRD. |
| Lactose | USP XXI |
| Rice starch | Ph. Eur. 2nd Ed. 1985 |
| Polysorbate 20 | Ph. Eur. 2nd Ed. 1985 |
| Calcium sulphate | NF XV |
| Titanium dioxide | Ph. Eur. 2nd Ed. 1985 |

Preparation of Diffusion Film-Coated Sucrose Crystals 4000 g of sucrose crystals were coated with a film coating mixture composed of 53.25 g of paraffin, 18.75 g of acetyltribytylcitrate. 350.25 g of ethyl cellulose, 5.25 g of colloidal silica and 7072.5 g of isopropanol according to the method disclosed in U.S. Pat. No. 4,572,833.

The resulting coated crystals were sieved through a 3 mm mesh sieve. 188 g of the crystals has a size of more than 3 mm and were discarded Preparation of Film-Coated Potassium Chloride Crystals 150 kg of potassium chloride crystals were coated with 140 kg of an inner film coating suspension composed of 195.8 kg of purified water, 1.3 kg of HPMC 5, 0.2 kg of antifoam emulsion, 0.27 kg of magnesium stearate, 2.43 kg of talc and 86.4 kg of Eudragit ® NE 30 D as well as with 15 kg of an outer film coating suspension composed of 13.5 kg of purified water, 0.75 kg of HPMC 5 and 0.75 kg of talc according to the method disclosed in European Published Specification No. 153 105.

The resulting coated crystals were sieved to a size fraction of 0.425–0.71 mm.

EXAMPLE 1

Preparation of a Pre-Mixed Gel and PVP-Coated Sucross Crystals

A pre-mixed gel was prepared from 2400 g of purified water, 125 g of Veegum ® PRO, 14.1 g of citric acid, 8.5 g of sodium citrate, 2.0 g of saccharin sodium and 3.0 g of sodium chloride.

The Veegum ® PRO was dispersed in the water at 7000 rpm on a PIL-MIX Lab. 0 Uni-V homogenizer at 40.50° C. for 15 min. This produced a viscous and highly thixotropic pale brown and creamy suspension. Citric acid, sodium citrate, saccharin sodium and sodium chloride were added as flavouring agents. These substances were dissolved in the premixed gel by further dispersion at 8000 rpm for 2 min. 100 g of diffusion film-coated sucrose crystals produced as described above were coated with a coating mixture composed of 3.0 g of HPMC 50 AB, 1.0 g of PVP, 1.0 g of propylens glycol and 100 g of purified water. The coating mixture was prepared by dissolving the HPMC 50 in the water at room temperature for about one hour on a magnetic stirrer (Struer type M 21) set at speed 8. The PVP was added and dissolved with continued stirring for about 5 min. after which propylene glycol was added. The coating mixture was then sieved through a 0.35 mm mesh sieve.

The coating of the sucrose crystals was carried out in a fluid bed (which had been pre-heated for 10 min.) in a manner known per se, at a rate of 3.5 g of the coating mixture/min., an inlet air temperature of 40°–45° C. and an outlet air temperature of 32°–35° C. The coated crystals were then dried for 5 min. at the same temperature and cooled. The entire coating procedure took 50 min. The resulting crystals had a white, shiny surface which under the microscope (magnification ×63) was observed to be slightly porous.

A ready-to-use composition may be prepared by carefully mixing 2.0 g of these coated crystals with 20.58 g of the pre-mixed gel prepared above for 5–10 seconds, producing a uniform distribution of the crystals in the gel and a slightly increased viscosity which became more pronounced with further stirring. When the viscous composition was carefully placed on a flat support and rinsed with water, the viscous medium could be separated from the crystals which were found to be surrounded by the pale brown gel. It was observed under the microscope (magnification ×40) that the crystals were surrounded by a ½-1 mm thick highly viscous gel.

This formulation made the crystals easy to swallow, and when a glass in which the composition had been poured was emptied they neither adhered to the glass nor to oral mucosa, contrary to film-coated crystals alone which partly remained in the glass where they had been mixed with water, and which adhered strongly to oral mucosa.

EXAMPLE 2

Preparation of a Pre-Mixed Gel and Coating of Potassium Chloride Crystals With a Swelling Coating 100 g of diffusion film-coated potassium chloride crystals which were prepared as described above were coated with a coating mixture composed of 4.5 g of HPMC 50 AB, 1.5 g of PEG 6000, 2.0 g of propylene glycol, 6.0 g of Polyplasdone XL and 300 g of purified water. The coating mixture was prepared by grinding the Polyplasdone carefully in a mortar followed by addition of the other solids to the mortar. The solids mixture was mixed with water at room temperature by dispersion for 2×10 min. at about 6000 rpm on a Silverson Laboratory mixer emulsifier model L2 air provided with a high shear screen and downthrust propeller. The propylene glycol was added during the final dispersion. The coating mixture was sieved through a 0.35 mm mesh sieve.

Coating of the film-coated potassium chloride crystals was carried out in a fluid bed (which had been pre-heated for 5 min.) in a manner known per se at a rate of 2.0 g of the coating mixture/min., an inlet air temperature of 43°-48° C. and an outlet air temperature of 34°-40° C. The coated crystals were dried for 5 min. at 50° C. The entire coating procedure took 180 min. The resulting crystals had a white, slightly matt surface which under the microscope (magnification×63) was observed to be porous and blistered.

A ready-to-use composition may be prepared by mixing 2.13 g of the potassium chloride crystals coated with a swelling coating with 21.07 g of a pre-mixed gel prepared as described in Example 1 for 5-10 seconds to produce a uniform distribution of the coated crystals in the viscous gel. When the composition was allowed to stand for 1-2 min., a highly viscous gel of the swollen coating and the gel could be observed. On further stirring the gel became more viscous, and the diffusion film-coated potassium chloride crystals could be observed in the gel. When the viscous composition was carefully placed on a flat support and rinsed with water, the viscous medium could be separated from the coated crystals which were found to be surrounded by the gel. It was observed under the microscope (magnification×40) that the crystals were surrounded by a ½-2 mm thick highly viscous gel.

This formulation made the crystals easy to swallow, and when a glass in which the composition had been poured was emptied they neither adhered to the glass nor to oral mucosa, contrary to film-coated crystals alone which partly remained in the glass where they had been mixed with water, and which adhered strongly to oral mucosa.

EXAMPLE 3

Preparation of a Powder Composition Containing Sodium Alginate and Sucross Crystals Costed With a Calcium Phosphate-Containing Coating 100 g of diffusion film-coated sucrose crystals prepared as described in Materials and Methods were coated with a coating mixture composed of 3.0 g of HPMC 50 AB, 1.0 g of propylene glycol, 2.4 g of calcium hydrogen phosphate, 0.8 g of PEG 6000 and 100 g of purified water.

The coating mixture was prepared by thoroughly grinding the HPMC and the calcium hydrogen phosphate in a mortar. Purified water was slowly added with vigorous stirring with a beater. Finally, PEG 6000 and propylene glycol were added with continued stirring for about 5 min. The coating mixture was sieved through a 0.35 mm mesh sieve.

The coating of the crystals was performed in a fluid bed (which had been pre-heated for 10 min.) in a manner known per se, at a rate of 3.5 g of the coating mixture/min., at inlet air temperature of 45°-47° C. and an outlet air temperature of 33.36° C. The coated crystals were dried at the same temperature for 5 min. The entire coating procedure took 50 min. The resulting crystals had a white, slightly matt surface which under the microscope (magnification x 63) was observed to be highly porous.

A powder component containing sodium alginate was prepared from 12.0 g of SOBALG FD 167, 6.0 g of SOBALG FD 170, 7.0 g of sodium hydrogen carbonate, 12.5 g of tartaric acid and 57.5 g of dextrose. These ingredients were thoroughly ground in a mortar.

Unit dosages of the dry composition were prepared by filling 0.72 g of this powder component and 1.0 g of the coated sucrose crystals into sachets No. 6.

A ready-to-use composition was prepared by adding the contents of a sachet to about 20 ml of purified water and stirring with a spoon for about 30 seconds. The mixture was allowed to stand for about 2 min. at room temperature followed by careful stirring for about 5 seconds to obtain a uniform distribution of the crystals in the resulting viscous medium.

When the viscous composition was carefully placed on a flat support and rinsed with water, the viscous medium could be separated from the crystals which were found to be surrounded by a cohesive sol. Under the microscope (magnification×40) the crystals were observed to be surrounded by a ½-2 mm thick clear sol.

This formulation made the crystals easy to swallow, and when a glass in which the composition had been poured was emptied they neither adhered to the glass nor to oral mucosa, contrary to film-coated crystals alone which partly remained in the glass where they had been mixed with water, and which adhered strongly to oral mucosa.

EXAMPLE 4

Preparation of a Powder Composition Containing Sodium Alginate and Acetylsalicylic Acid Crystals Coated With a Swelling Calcium Hydrogen Phosphate-Containing Coating 100 g of acetylsalicylic acid crystals were coated with a coating mixture composed of 1.5 g of HPMC 15, 1.5 g of HPMC 50 AB, 1.0 g of propylene glycol, 0.8 g of PEG 6000, 2.4 g of calcium hydrogen phosphate, 2.0 g of Avicel ® PH 101 and 100 g of purified water.

The coating mixture was prepared by slowly adding purified water to the two HPMC grades with vigorous stirring with a beater. Avicel® PH and PEG 6000 were added with continued stirring for 5 min. after which the suspension was dispersed as described in Example 2. Propylene glycol and calcium hydrogen phosphate were added with continued dispersion for 1 min. as described in Example 2. The coating mixture was sieved through a 0.35 mm mesh sieve.

The coating of the crystals was performed in a fluid bed (which had been pre-heated for 10 min.) in a manner known per se, at a rate of 3.5 g of the coating mixture/min., an inlet air temperature of 44°–45° C. and an outlet air temperature of 35°–36° C. The coated crystals were dried for 5 min. The crystals were then sieved through a 0.5 mm mesh sieve. The resulting crystals had a white, matt surface which under the microscope (magnification×63) was observed to be grainy and porous. Furthermore, the crystals had formed small agglomerates.

The coated crystals were mixed with a powder component containing sodium alginate prepared as described in Example 3 at the dosage level indicated in Example 3.

A ready-to-use composition was prepared from the dry mixture as described in Example 3 with the exception that the composition was stirred for 1 minute and allowed to stand at room temperature for about 30 seconds.

When the viscous composition was placed on a flat support and rinsed with water, the viscous medium could be separated from the crystals which were found to be surrounded by a cohesive sol. Under the microscope (magnification×40) the crystals were observed to be sur rounded by a ½-2 mm thick clear sol.

This formulation made the crystals easy to swallow, and when a glass in which the composition had been poured was emptied they neither adhered to the glass nor to oral mucosa, contrary to film-coated crystals alone which partly remained in the glass where they had been mixed with water, and which adhered strongly to oral mucosa.

EXAMPLE 5

Preparation of a Tablet Composition Containing Sodium Alginate, Alginic Acid and Potassium Chloride Crystals Coated With a Calcium Sulphata-Containing Film 100 g KCl crystals were coated with 86.7 g of a diffusion film coating suspension containing 0.56 g of HPMC 5, 0.12 g of magnesium stearate, 1.05 g of talc, 47.47 g of purified water and 37.5 g of Eudragit® NE 30D. The film coating suspension was prepared and coated on the crystals according to the method disclosed in the European published specification No. 153 105.

The resulting coated crystals were then coated with 20 g of a coating suspension containing 13.04 g of purified water, 2.5 g of calcium sulphate, 0.20 g of PVP, 0.01 g of antifoam emulsion, 0.03 g of polysorbate 20 and 4.22 g of Eudragit® NE 30 D.

The film coating suspension was prepared by dispersing (vide Example 2) calcium sulphata and PVP in purified water at a temperature of about 60° C. After cooling, the dispersion was continued for a further 10 minutes. The remaining ingredients were admixed with continuous stirring on a magnetic stirrer (Struer type M 21) set at speed 3.

The crystals were coated and hardened according to the method disclosed in European published specification No. 153 105 and Example 4.

The coated crystals were sieved to a fraction of 0.41–1.18 mm. The resulting crystals had a pale grey, matt surface which under the microscope (magnification×63) was observed to be slightly grainy, but otherwise clear and translucent.

A granulate was prepared from 3.2 g of sodium bicarbonate and 20 g of SOBALG FD 160. 21 g of liquid composed of 0.6 g PVP dissolved in 16.2 g purified water and 4.2 g of isopropanol was used as the granulation liquid. The moistened components were sieved (0.71 mm) and dried at 40° C. for 3 hours. The granulate was sieved (0.71 mm) before use.

A powder component composed of 2.0 g of citric acid (as the powdered monohydrate thereof), 14.0 g sieved (0.3 mm) of titanium dioxide, 2.0 g of SOBALG PH 060, 0.6 g of colloidal silica, 1.6 g of powdered saccharine sodium and 56.0 g of Avicel® PH 101 were mixed for 10 minutes in a small cube mixer (Erweka type AR 400, 3.5 liter).

The powder, granulate and 100 g of coated crystals were mixed for 5 minutes in a cube mixer. The mixture was compressed into capsule-shaped tablets (breaking strength: about 130 N, gross weight: 2.00 g) in an excentric press (Diaf type TM-20). A ready-to-use composition was prepared by stirring one tablet in 20 ml of cold (about 13° C.) tap water by means of a spoon. The composition was stirred for about 70 seconds resulting in the formation of a viscous medium. When the viscous composition was placed on a flat support and rinsed carefully with water, the viscous medium could be separated from the coated crystals which were found to be surrounded a white, cohesive sol. No residues of a tablet core were observed. Under the microscope (magnification×40) it was observed that the crystals were surrounded by a ½-2 mm thick, white sol.

This formulation made the crystals easy to swallow, and when a glass in which the composition had been poured was emptied they neither adhered to the glass nor to oral mucosa, contrary to film-coated crystals alone which partly remained in the glass where they had been mixed with water, and which adhered strongly to oral mucosa.

EXAMPLE 6

Preparation of a powder composition, calcium sulphate-coated sucrose crystals and calcium sulphate-coated placebo microcapsules 250 g of placebo microcapsules were prepared by extrusion (0.8 mm, Nica model 605.14) and spheronization for 30 sec. at 800 rpm (diameter of bottom plate: 25 cm) in accordance with conventional methods. The microcapsules were composed of 50 g Avicals PH 101 and 200 g of lactose. The powders were mixed and moistened with 70 g of purified water in a Kenwood mixer. The microcapsules were dried at 40° C. in a drying cupboard for 4 hours and sieved (0.41–1.18 mm).

100 g of sucrose crystals which had been diffusion film coated as described in Materials and Methods and 100 g of placebo microcapsules, respectively, were coated with a calcium sulphate-containing coating suspension as described in Example 5 and sieved (0.425–3.0 mm and 0.425–1.18 mm, respectively).

A powder component composed of 90 g SOBALG FD 160, 34.5 g of tartaric acid, 59.9 g of rice starch, 71.8 g of sieved (0.3 mm) titanium dioxide, 8.2 g of sodium citrate, 28.0 g of sodium bicarbonate, 6.0 g PEG 6000 and 2.0 g of saccharine sodium was prepared as follows: Rice starch, titanium dioxide, sodium citrate, sodium bicarbonate, PEG 6000 and saccharine sodium were ground in a Fritch Pulverisette model 14 (0.2 mm screen and high speed). The resulting powder was mixed with SOBALG FD 160 and tartaric acid for 10 minutes in a small cube mixer as described in Example 5.

The sucrose crystals and placebo microcapsules and powder component were stored in separate containers before use.

1.5 ml of powder, 1.0 ml of coated sucrose crystals and 1.0 ml of coated placebo microcapsules were added to a small beaker (max 5 ml). The 3 components were transferred to a 100 ml beaker. A ready-for-use composition was prepared by adding 30 ml of cold tap water and stirring with a spoon for about 60 sec. The resulting viscous composition was immediately placed on a flat support and rinsed carefully with water, whereby the viscous medium was separated from the crystals and microcapsules which were found to be surrounded by a white, cohesive sol. Under the microscope (magnification ×40) it was observed that the crystals and microcapsules were surrounded by a ½–2 mm thick white sol.

This formulation made the crystals easy to swallow and when a glass in which the composition had been poured was emptied they neither adhered to the glass nor to oral mucosa, contrary to film-coated crystals alone which partly remained in the glass where they had been mixed with water and which adhered strongly to oral mucosa.

Furthermore, 1.5 ml of the powder component and 2.5 ml of the coated microcapsules were stirred in 30 ml of cold tap water for about 60 sec., whereby similar results were obtained as described above.

I claim:

1. An oral composition comprising a dispersion in an aqueous carrier of a multiplicity of solid particles having particle sizes of about 0.05–7 mm and shapes such that they normally feel gritty, the particles:
   (a) containing at least one active substance selected from the group consisting of drugs, vitamins, nutrients, and combinations thereof; and
   (b) being provided with an aqueous masking surface layer having a higher viscosity than the viscosity of the surrounding aqueous carrier, the masking surface layer being provided by a first viscosity-increasing agent comprising a gelling or swelling agent, being in intimate contact with the surfaces of the solid particles and thereby reducing the grittiness of said particles, contributing to masking any unpleasant taste of the active substance, and/or reducing the tendency of the particles to settle, to adhere to a container from which the composition is administered, or to adhere to the oral mucosa;
   the dispersion containing about 0.05–20 weight percent of the gelling or swelling agent; and
   the dispersion additionally containing a second viscosity-increasing agent which is distinct from the gelling or swelling agent and is selected from the group consisting of:
   (i) a substance having a redox potential such that, in the aqueous medium it is oxidized or reduced;
   (ii) a substance which forms a salt or chelate with the gelling or swelling agent dispersed in said aqueous medium;
   (iii) a surfactant which reduces the surface tension of the water in said aqueous medium; and
   (iv) combinations thereof.

2. The oral composition of claim 1, in which the gelling or swelling agent or agents are selected from the group consisting of:
   (1) a starch selected from the group consisting of corn starch, potato starch, and combinations thereof;
   (2) a hydrophilic polymer selected from the group consisting of pectin, agar, dextran, carrageenan, tragacanth gum, locust bean gum, acacia gum, guar gum, xanthan gum, ghatti gum, alginic acid, sodium alginate, and combinations thereof;
   (3) as cellulose derivative selected from the group consisting of methylcellulose, carboxymethylcellulose, sodium starch glycollate, sodium or calcium carboxymethylcellulose, hydroxyethyl methylcellulose, hydroxypropyl methylcellulose, ethylcellulose, ethylhydroxy ethylcellulose, ethylmethylcelluylose, hydroxyethylcellulose, cellulose acetate phthalate, microcrystalline cellulose, and combinations thereof;
   (4) silica, aluminum silicate, magnesium silicate, aluminum magnesium silicate, sodium silicate, felspar, and combinations thereof;
   (5) aluminum hydroxide;
   (6) a protein selected from the group consisting of gelatin, casein and combinations thereof;
   (7) a polymer selected from the group consisting of an acrylate, carboxypolymethylene, a polyalkylene glycol, a polyvinylpyrrolidone, and combinations thereof; and
   (8) combinations thereof.

3. An oral composition according to claim 1, in which the second viscosity-increasing agent is a material which forms a salt or a chelate with the gelling or swelling agent constituting the first viscosity-increasing agent.

4. The oral composition of claim 1, wherein the second viscosity-increasing agent is a salt-forming material incorporating a mono-, di- or trivalent cation selected from the group consisting of LI, Na, K, Mg, Ca, Zn, Cu, Fe, Cr, Ni, Mn, Al, $NH_4$, and combinations thereof.

5. The oral composition of claim 1, wherein the second viscosity-increasing agent is a salt-forming material incorporating a mono-, di- or trivalent anion selected from the group consisting of Cl, Br, $SO_4$, $PO_4$, $NO_3$, $CO_3$, and combinations thereof.

6. The oral composition of claim 1, wherein the second viscosity-increasing agent is a salt-forming material incorporating a mono-, di- or trivalent anion of a carboxylic acid selected from the group consisting of lactic, acetic, citric, acetylsalicylic, benzoic, alginic, malic, stearic, palmitic, ascorbic and galacturonic acid, and combinations thereof; and an amino acid selected from the group consisting of glutamic acid, aspartic acid, glycine, and combinations thereof.

7. The oral composition of claim 1, wherein the second viscosity-increasing agent is a chelate-forming material selected from the group consisting of EDTA, polyoxyethylenes, peptides, proteins, starch, cellulose derivatives, polyesters, and combinations thereof.

8. The oral composition of claim 1, wherein the second viscosity-increasing agent is incorporated in a coating provided on the solid particles.

9. A method of preparing a ready-to-use oral composition comprising a dispersion in an aqueous carrier of a multiplicity of solid particles having particle sizes of about 0.5–7 mm and shapes such that they normally feel gritty, the method comprising:

(a) providing an aqueous carrier; and
(b) prior to administration, dispersing in the aqueous carrier, a multiplicity of particles comprising:
(1) at least one active substance selected from the group consisting of drugs, vitamins, nutrients and combinations thereof; and
(2) a viscosity-increasing agent selected from the group consisting of
(i) a first viscosity-increasing agent comprising a gelling or swelling agent; and
(ii) a second viscosity-increasing agent which is distinct form the gelling or swelling agent and is selected from the group consisting of a substance having a redox potential such that, in the aqueous carrier, it is oxidized or reduced; a substance which forms a salt or chelate with a gelling or swelling agent dispersed in said aqueous medium; a surfactant which reduces the surface tension of the water in said aqueous medium; and combinations thereof;

the resulting dispersion containing about 0.05–20 weight percent of a gelling or swelling agent or agents;
said agent(s) providing an aqueous masking surface layer on the particles, the masking surface layer having a higher viscosity than the viscosity of the surrounding aqueous carrier, being in intimate contact with the surfaces of the solid particles and thereby reducing the grittiness of said particles, contributing to masking any unpleasant taste of the active substance, and/or reducing the tendency of the particles to settle, to adhere to a container from which the composition is administered, or to adhere to the oral mucosa.

10. A method according to claim 9, wherein the second viscosity-increasing agent is a material which forms a salt or a chelate with the gelling or swelling agent constituting the first viscosity-increasing agent.

11. A method according to claim 9, wherein the second viscosity-increasing agent is a salt-forming material incorporating a mono-, di- or trivalent cation selected from the group consisting of ions of Li, Na, K, Mg, Ca, Zn, Cu, Fe, Cr, Ni, Mn, A, $NH_4$, and combinations thereof.

12. A method according to claim 9, wherein the second viscosity-increasing agent is a salt-forming material incorporating a mono-, di- or trivalent anion selected from the group consisting of Cl, Br, $SO_{43}$, $PO_4$, $NO_3$, $CO_3$, and combinations thereof.

13. A method according to claim 9, wherein the second viscosity-increasing agent is a salt-forming material incorporating a mono-, di- or trivalent anion of a carboxylic acid selected from the group consisting of lactic, acetic, citric, acetylsalicylic, benzoic, alginic, malic, stearic, palmitic, ascorbic and galacturonic acid and combinations thereof; and an amino acid selected from the group consisting of glutamic acid, aspartic acid, glycine, and combinations thereof.

14. A method according to claim 9, wherein the viscosity-increasing agent in the particles is a chelate-forming material selected from the group consisting of EDTA, polyoxyethylenes, peptides, proteins, starch, cellulose derivatives selected from the group consisting of sodium or calcium carboxymethylcellulose, methylcellulose, ethylcellulose, ethylhydroxyethylcellulose, microcrystalline cellulose, ethylmethylcellulose, hydroxyethylcellulose, hydroxyethylmethylcellulose, and cellulose acetate phthalate, polyesters, and combinations thereof.

15. A method according to claim 9, wherein the second viscosity-increasing agent is incorporated in a coating provided on the solid particles.

16. The method of claim 9, wherein the gelling or swelling agent or agents are selected from the group consisting of:
(1) a starch selected from the group consisting of corn starch, potato starch and combinations thereof;
(2) a hydrophilic polymer selected from the group consisting of pectin, agar, dextran, carrageenan, tragacanth gum, locust bean gum, acacia gum, guar gum, xanthan gum, ghatti gum, alginic acid, sodium alginate and combinations thereof;
(3) a cellulose derivative selected from the group consisting of methylcellulose, carboxymethylcellulose, sodium starch glycollate, sodium or calcium carboxymethylcellulose, hydroxyethyl methylcellulose, hydroxypropyl methylcellulose, ethylcellulose, ethylhydroxy ethylcellulose, ethylmethylcellulose, hydroxyethylcellulose, cellulose acetate phthalate, microcrystalline cellulose and combinations thereof;
(4) silica, aluminum silicate, magnesium silicate, aluminum magnesium silicate, sodium silicate, felspar and combinations thereof;
(5) aluminum hydroxide;
(6) a protein selected from the group consisting of gelatin or casein;
(7) a polymer selected from the group consisting of an acrylate, carboxypolymethylene, a polyalkylene glycol, a polyvinylpyrrolidone, and combinations thereof; and
(8) combinations thereof.

* * * * *